(12) United States Patent
Mou et al.

(10) Patent No.: US 11,298,032 B2
(45) Date of Patent: *Apr. 12, 2022

(54) WEARABLE BLOOD PRESSURE MEASURING DEVICE

(71) Applicant: Microjet Technology Co., Ltd., Hsinchu (TW)

(72) Inventors: Hao-Jan Mou, Hsinchu (TW); Ta-Wei Hsueh, Hsinchu (TW); Yung-Lung Han, Hsinchu (TW); Chi-Feng Huang, Hsinchu (TW); Wei-Ming Lee, Hsinchu (TW); Hsuan-Kai Chen, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 317 days.

This patent is subject to a terminal disclaimer.

(21) Appl. No.: 16/164,084

(22) Filed: Oct. 18, 2018

(65) Prior Publication Data

US 2019/0133455 A1 May 9, 2019

(30) Foreign Application Priority Data

Nov. 7, 2017 (TW) .................................. 106138514

(51) Int. Cl.
*A61B 5/022* (2006.01)
*A61B 5/00* (2006.01)
(Continued)

(52) U.S. Cl.
CPC ............ *A61B 5/022* (2013.01); *A61B 5/0235* (2013.01); *A61B 5/02241* (2013.01);
(Continued)

(58) Field of Classification Search
CPC . A61B 5/022; A61B 5/02241; A61B 5/02208; A61B 5/02233; A61B 5/0225;
(Continued)

(56) References Cited

U.S. PATENT DOCUMENTS 4,896,676 A * 1/1990 Sasaki ................ A61B 5/02241
600/494
2008/0177187 A1* 7/2008 Lee .................... A61B 5/02233
600/490
(Continued)

FOREIGN PATENT DOCUMENTS

CN 101103906 B 7/2010
CN 203488347 U 3/2014
(Continued)

OTHER PUBLICATIONS

Extended European Search Report dated Mar. 27, 2019 for Application No. 18201151.0.

*Primary Examiner* — Eric J Messersmith
(74) *Attorney, Agent, or Firm* — Birch, Stewart, Kolasch & Birch, LLP (57) ABSTRACT

A wearable blood pressure measuring device includes a strap structure, a micro gas pump and a pressure sensor. The strap structure is adapted to be worn by a user and has an outer surface and an inner surface. The micro gas pump is disposed on the strap structure. The pressure sensor is combined with the micro gas pump through an elastic medium, disposed on the inner surface of the strap structure and in contact with skin of the user for monitoring blood pressure. The micro gas pump is operated to drive gas, wherein the gas is transported into the elastic medium to inflate the elastic medium with the gas. The expanded elastic medium pushes the pressure sensor to press against the skin of the user for facilitating measurement of a blood pressure of a target artery by a flattening and scanning operation.

10 Claims, 13 Drawing Sheets

(51) Int. Cl.
*A61B 5/0235* (2006.01)
*A61B 5/021* (2006.01)
*A61B 5/024* (2006.01)

(52) U.S. Cl.
CPC .......... *A61B 5/681* (2013.01); *A61B 5/02141* (2013.01); *A61B 5/02438* (2013.01); *A61B 5/6824* (2013.01); *A61B 5/6831* (2013.01); *A61B 2560/0406* (2013.01); *A61B 2562/0247* (2013.01)

(58) Field of Classification Search
CPC ... A61B 5/02255; A61B 5/681; A61B 5/6824; A61B 5/6825; A61B 5/6826; A61B 5/6831; A61B 5/6828; A61B 5/6829
See application file for complete search history.

(56) References Cited

U.S. PATENT DOCUMENTS

| | | | | |
|---|---|---|---|---|
| 2015/0335282 | A1* | 11/2015 | Lee | A61B 5/681 600/499 |
| 2016/0235307 | A1* | 8/2016 | Chou | A61B 5/0245 |
| 2016/0287103 | A1* | 10/2016 | Saponas | A61B 5/681 |
| 2017/0222125 | A1* | 8/2017 | Chen | F04B 45/047 |
| 2017/0340210 | A1* | 11/2017 | Chuang | A61B 5/681 |
| 2018/0085058 | A1* | 3/2018 | Chakravarthi | A61B 5/150022 |
| 2018/0140209 | A1* | 5/2018 | Ono | A61B 5/022 |
| 2018/0160988 | A1* | 6/2018 | Miller | H04B 1/385 |
| 2019/0298181 | A1* | 10/2019 | Iwata | A61B 5/681 |
| 2020/0178812 | A1* | 6/2020 | Zhang | A61B 5/6801 |

FOREIGN PATENT DOCUMENTS

| | | |
|---|---|---|
| CN | 104234986 A | 12/2014 |
| CN | 104235081 A | 12/2014 |
| CN | 205383064 U | 7/2016 |
| CN | 205458646 U | 8/2016 |
| CN | 205714691 U | 11/2016 |
| CN | 205744376 U | 11/2016 |
| CN | 205918569 U | 2/2017 |
| CN | 206129568 U | 4/2017 |
| CN | 206211877 U | 5/2017 |
| CN | 106974632 A | 7/2017 |
| CN | 107037178 A | 8/2017 |
| CN | 206439166 U | 8/2017 |
| CN | 206585604 U | 10/2017 |
| CN | 209018719 U | 6/2019 |
| EP | 3 203 076 A1 | 8/2017 |
| KR | 10-2009-0029556 A | 3/2009 |
| TW | M523432 U | 6/2016 |
| TW | M529698 U | 10/2016 |
| TW | I572328 B | 3/2017 |
| WO | WO 2016/161226 A1 | 10/2016 |
| WO | WO-2016161226 A1 * | 10/2016 ........... A61B 5/6831 |

* cited by examiner

WEARABLE BLOOD PRESSURE MEASURING DEVICE

FIELD OF THE INVENTION

The present disclosure relates to a wearable blood pressure measuring device, and more particularly to a wearable blood pressure measuring device having a micro gas pump, an elastic medium and a pressure sensor combined together.

BACKGROUND OF THE INVENTION

Nowadays, the pursuit of efficiency and the personal pressure are growing and the awareness of the pursuit of personal health is gradually developing. Thus, the ordinary people will want to regularly monitor or examine their own health conditions. In general, the conventional data measurement of human physiological health information is mainly obtained through a fixed sphygmomanometer or a large-scale detection instrument, which usually includes components such as a motor-driven gas pump, an airbag, a sensor and a gas-releasing valve and a battery. The motor-driven gas pump is prone to generate the frictional loss, and the assembled components thereof are bulky. It is not conducive to regular use. Moreover, if a miniature-sized motor-driven gas pump is used, the frictional loss will be increased and more energy will be consumed.

In order to facilitate the ordinary people to regularly monitor their own health conditions and allow the monitoring device to be carried easily, many wearable health monitoring devices are introduced into the market. In view of the common wearable health monitoring devices on the market, they are used for measuring the health conditions by an optical detection method. However, the precision of the optical detection method is not high enough and it often results in an error value to be generated. Reliable data cannot be obtained effectively. As a result, the users cannot obtain accurate and relevant data about their health, so that the users may misjudge their health conditions.

Generally speaking, in order to measure physiological information of a person to be tested, a specified position such as the head, the heart part, the wrist or the ankle is usually selected to be monitored. The positions mentioned above are the most sensible in the human body for monitoring information such as pulse blood pressure and heartbeat. By monitoring at the positions, the physiological health information of the person to be tested can be understood quickly and effectively. However, as mentioned above, if the wearable health monitoring device with the optical detection method is used, the precision of the optical detection method is not high enough so that the measured data is usually not reliable. If the commercially-available sphygmomanometers or other measuring instruments with higher reliability are used, the instruments have bulky volume and fail to meet the requirements of light weightiness, thinning and easy portability.

Therefore, there is a need of providing a wearable blood pressure measuring device to address the above-mentioned issues. The wearable blood pressure measuring device is small-sized, miniaturized, portable, power-saving, high-precise and facilitated for personal health monitoring device.

SUMMARY OF THE INVENTION

An object of the present disclosure is to provide a wearable blood pressure measuring device having a micro gas pump, an elastic medium and a pressure sensor combined together. By transporting gas to the elastic medium through a piezoelectrically actuated micro gas pump, the elastic medium is inflated with gas and expanded. Then, the pressure sensor disposed relative to the elastic medium is pressed against the user's body and utilized to measure the blood pressure information of the user. Thus, it solves the problems of the measuring instrument used in the prior art, which has a large volume, is difficult to be thinned, consumes much power and cannot achieve the purpose of being portable. At the same time, it further solves the problem of low precision caused by the health monitoring device in the prior art, which detects through the optical detection method.

In accordance with an aspect of the present disclosure, a wearable blood pressure measuring device includes a strap structure, a micro gas pump and a pressure sensor. The strap structure is adapted to be worn by a user and has an outer surface and an inner surface. The micro gas pump is disposed on the strap structure. The pressure sensor is combined with the micro gas pump through an elastic medium, disposed on the inner surface of the strap structure and in contact with skin of the user for monitoring blood pressure. The micro gas pump is operated to drive gas, so that the gas is transported into the elastic medium, and the elastic medium is inflated with the gas to be expanded. The expansion of the elastic medium pushes the pressure sensor to press against the skin of the user, so that the pressure sensor can measure a blood pressure of a target artery by a flattening and scanning operation.

The above contents of the present disclosure will become more readily apparent to those ordinarily skilled in the art after reviewing the following detailed description and accompanying drawings, in which:

DETAILED DESCRIPTION OF THE PREFERRED EMBODIMENT

The present disclosure will now be described more specifically with reference to the following embodiments. It is to be noted that the following descriptions of preferred embodiments of this disclosure are presented herein for purpose of illustration and description only. It is not intended to be exhaustive or to be limited to the precise form disclosed.

Figure 2A:
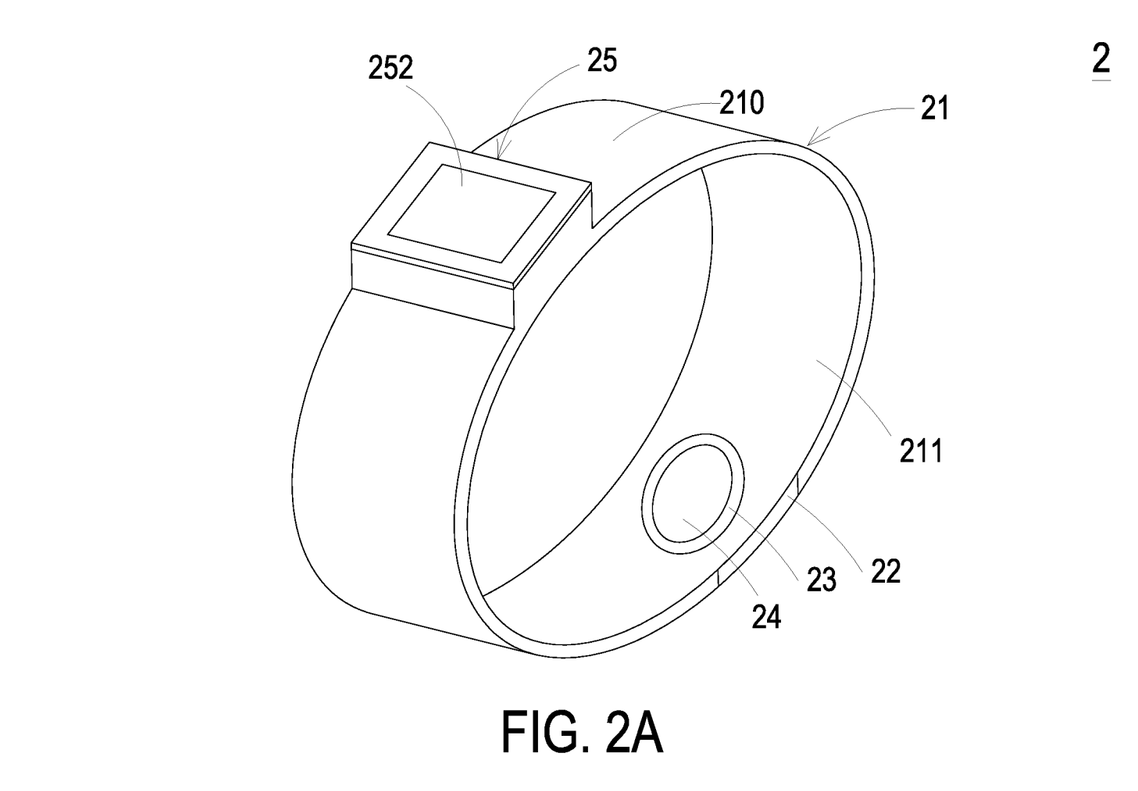
FIG. 2A is a schematic structural view illustrating a wearable blood pressure measuring device according an embodiment of the present disclosure.

Please refer to FIG. 2A. The present discourse provides a wearable blood pressure measuring device 2 including at least one strap structure 21, at least one micro gas pump 22, at least one pressure sensor 24, and at least one elastic medium 23. The number of the strap structure 21, the micro gas pump 22, the pressure sensor 24 and the elastic medium 23 is exemplified by one for each in the following embodiments but not limited thereto. It is noted that each of the strap structure 21, the micro gas pump 22, the pressure sensor 24 and the elastic medium 23 can also be provided in plural numbers.

Figure 1:
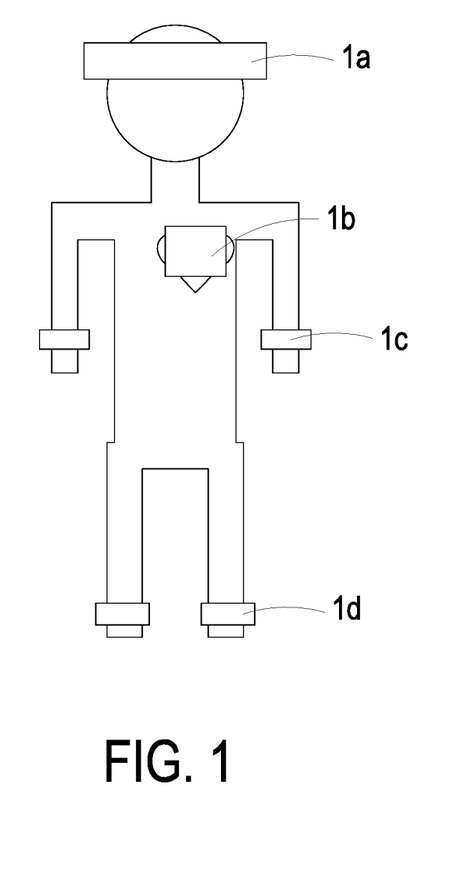
FIG. 1 is a schematic structural view illustrating positions for measuring physiological information of the user to be tested according to the prior art.

Please refer to FIGS. 1 to 6. The wearable blood pressure measuring device 2 of the present disclosure is provided to be worn on a specific to-be-measured position of a user, in which the specific position can be for example as shown in FIG. 1 and located at the head 1a, the chest area 1b, the wrist 1c, the ankle 1d or other specific to-be-measured parts, but not limited thereto. Referring to FIG. 2A, in an embodiment of the present disclosure, the wearable blood pressure measuring device 2 includes a strap structure 21, a micro gas pump 22, an elastic medium 23, a pressure sensor 24 and a driving-and-control module 25. The strap structure 21 has an outer surface 210 and an inner surface 211, and the outer surface 210 is opposite to the inner surface 211. The micro gas pump 22 is embedded in the strap structure 21 while being exposed on the inner surface 211. The elastic medium 23 has a first surface 23a and a second surface 23c, the first surface 23a has an opening 23b communicating with a gas-collecting perforation 228a of the micro gas pump 22 and in fluid communication with the micro gas pump 22. The pressure sensor 24 is disposed on the second surface 23c of the elastic medium 23 and combined with the micro gas pump 22 through the elastic medium 23. The elastic medium 23 and the pressure sensor 24 are both disposed on the inner surface 211 of the strap structure 21. The pressure sensor 24 is in contact with skin 11c of the user for measuring blood pressure and accordingly generating blood pressure information, wherein the blood pressure information may be transmitted to the driving-and-control module 25 for recording. The driving-and-control module 25 is also disposed on the strap structure 21. For example, the driving-and-control module 25 may include a controlling circuitry (not shown) for controlling the operation of the micro gas pump 22 and receiving the blood pressure information from the pressure sensor 24, but not limited thereto. The elastic medium 23 can be for example an airbag, but not limited thereto.

Referring to FIG. 1 and FIG. 2A, the strap structure 21 of the wearable blood pressure measuring device 2 can be a ring-shaped strip structure made of a soft material or a hard material, such as silicone rubber, plastic material, webbing material, towel material, leather material, metal material or any other operable materials. The strap structure 21 is mainly used to wrap around a specific position of the user, for example the wrist 1c or the ankle 1d, but not limited thereto. The length of the strap structure 21 is not limited herein. In some embodiments, the strap structure 21 can also be a sleeve made of a long webbing material or a towel material, so as to be worn on the head 1a of the user. Alternatively, in some other embodiments, the strap structure 21 can also be an auxiliary fixing tape made of a longer plastic material, so as to be worn around the chest area 1b of the user for monitoring the physiological information of the user's heart. As to the connection means of the two ends of the strip structure 21, they can be attached to each other by hook-and-loop fasteners, the convex-and-concave joints, or the fastening ring commonly used in watch strap. Alternatively, a ring structure integrally formed in one piece or the like may be used. The connection means is adjustable according to the practical requirement, but not limited thereto.

The strap structure 21 of the wearable blood pressure measuring device 2 is not only used to wrap around a specific position of the user, but also utilized to carry the micro gas pump 22 and the driving-and-control module 25 thereon. As described above, the driving-and-control module 25 is connected to and disposed on the outer surface 210 of the strap structure 21. The driving-and-control module 25 can be integrally formed with the strap structure 21 or fastened on the strap structure 21. The present disclosure is not limited thereto.

Figure 2B:
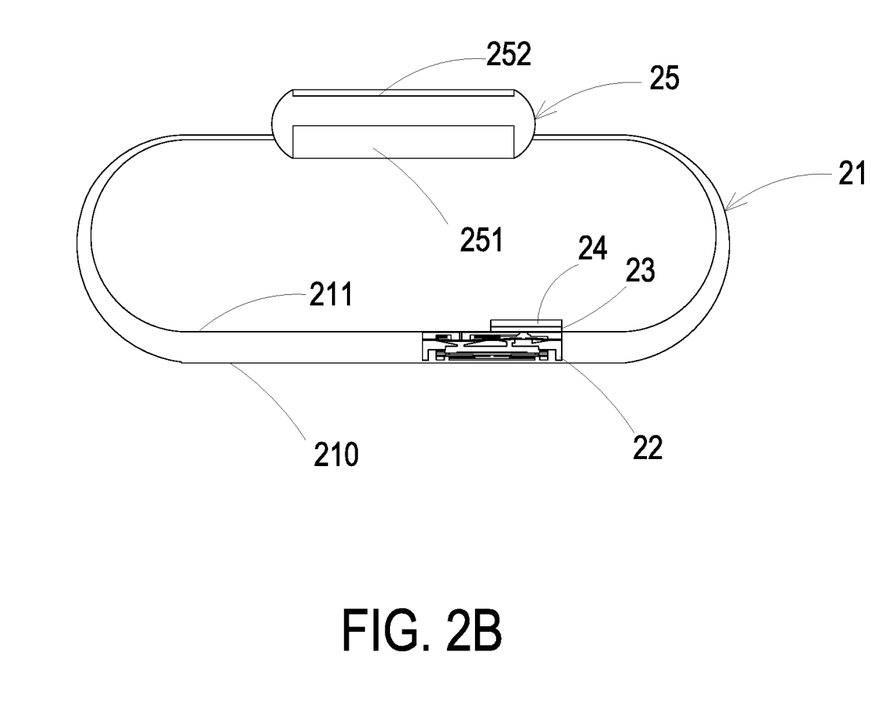
FIG. 2B is a cross sectional view illustrating related components of the wearable blood pressure measuring device according to the embodiment of the present disclosure.

Please refer to FIGS. 2A and 2B. In some embodiments, the wearable blood pressure measuring device 2 further includes a transmission module 251 and a display screen 252 disposed on the driving-and-control module 25. The display screen 252 may be utilized to display the blood pressure information. In some other embodiments, the wearable blood pressure measuring device 2 further has a protective cover (not shown) which covers the driving-and-control module 25 and may cover an extent of the driving-and-control module 25 over the display screen 252. The display screen 252 may be a touch screen through which the user can select the information to be displayed. The information can be at least one selected from the group consisting of the blood pressure information of the user, the time information and the caller information.

Figure 3:
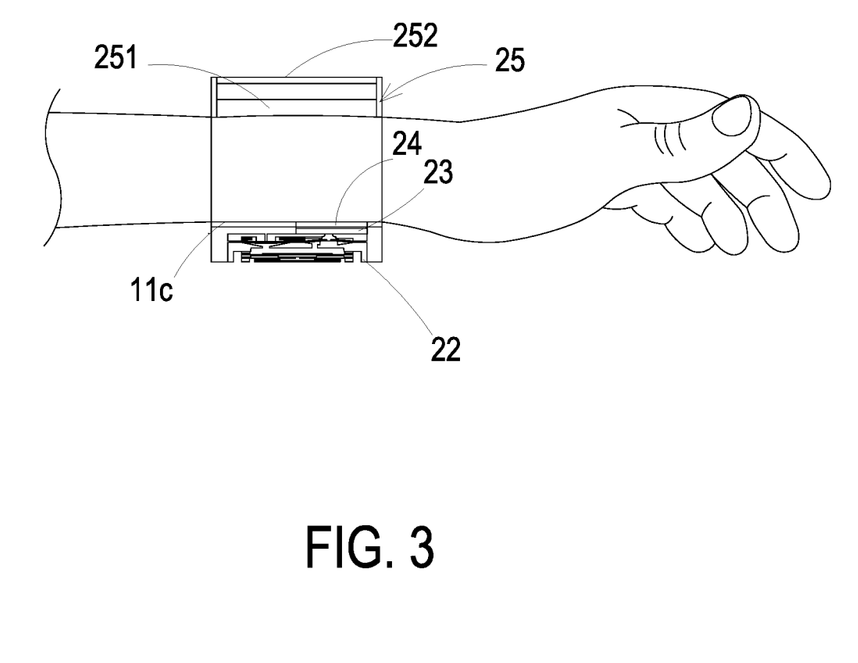
FIG. 3 shows the wearable blood pressure measuring device of the present disclosure worn on a user.

Please refer to FIG. 3. When the user operates the driving-and-control module 25 through the display screen 252, since the driving-and-control module 25 is electrically connected to the micro gas pump 22 through a conductive wire (not shown) disposed within the strap structure 21, the actuation of the micro gas pump 22 can be controlled. The actuation of the micro gas pump 22 makes the gas inhaled into the elastic medium 23 from the external environment, and the elastic medium 23 is inflated with the gas and expanded. The expanded elastic medium raises up the pressure sensor 24 which is disposed thereon. Consequently, the pressure sensor 24 abuts against and contacts with the skin 11c of the user, and measures the blood pressure of the user.

Figure 4:
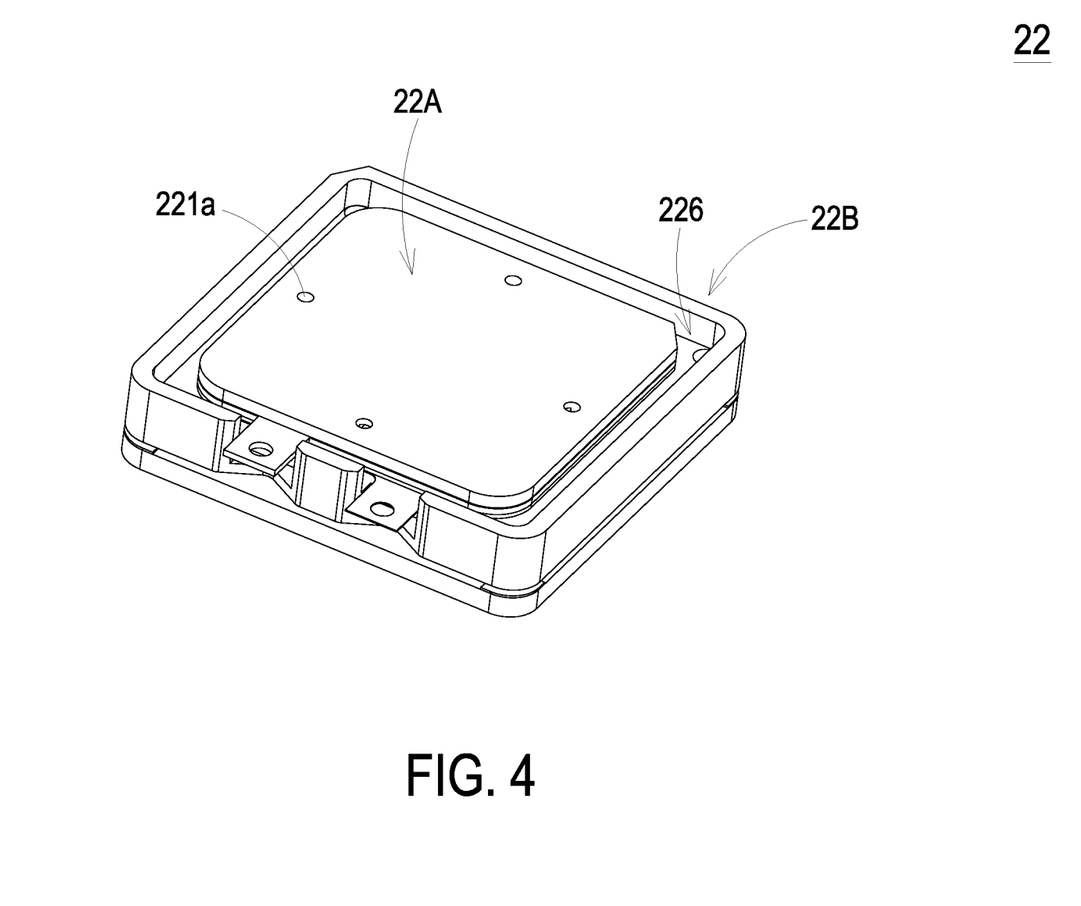
FIG. 4 is a schematic structural view illustrating a micro gas pump of the wearable blood pressure measuring device according to an embodiment of the present disclosure.
Figure 5:
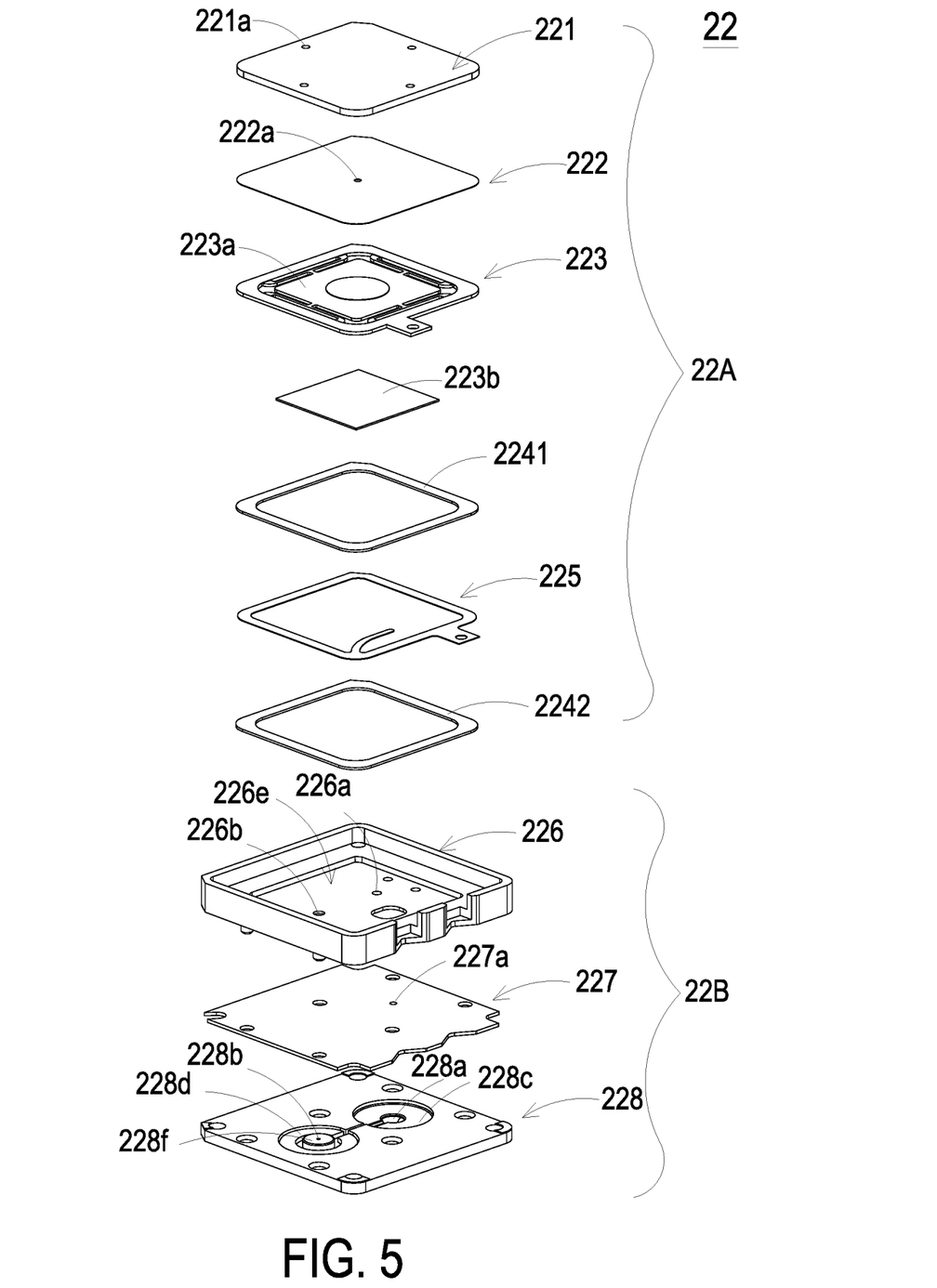
FIG. 5 is a disassembled structural view illustrating the micro gas pump of the wearable blood pressure measuring device of FIG. 4.
Figure 6:
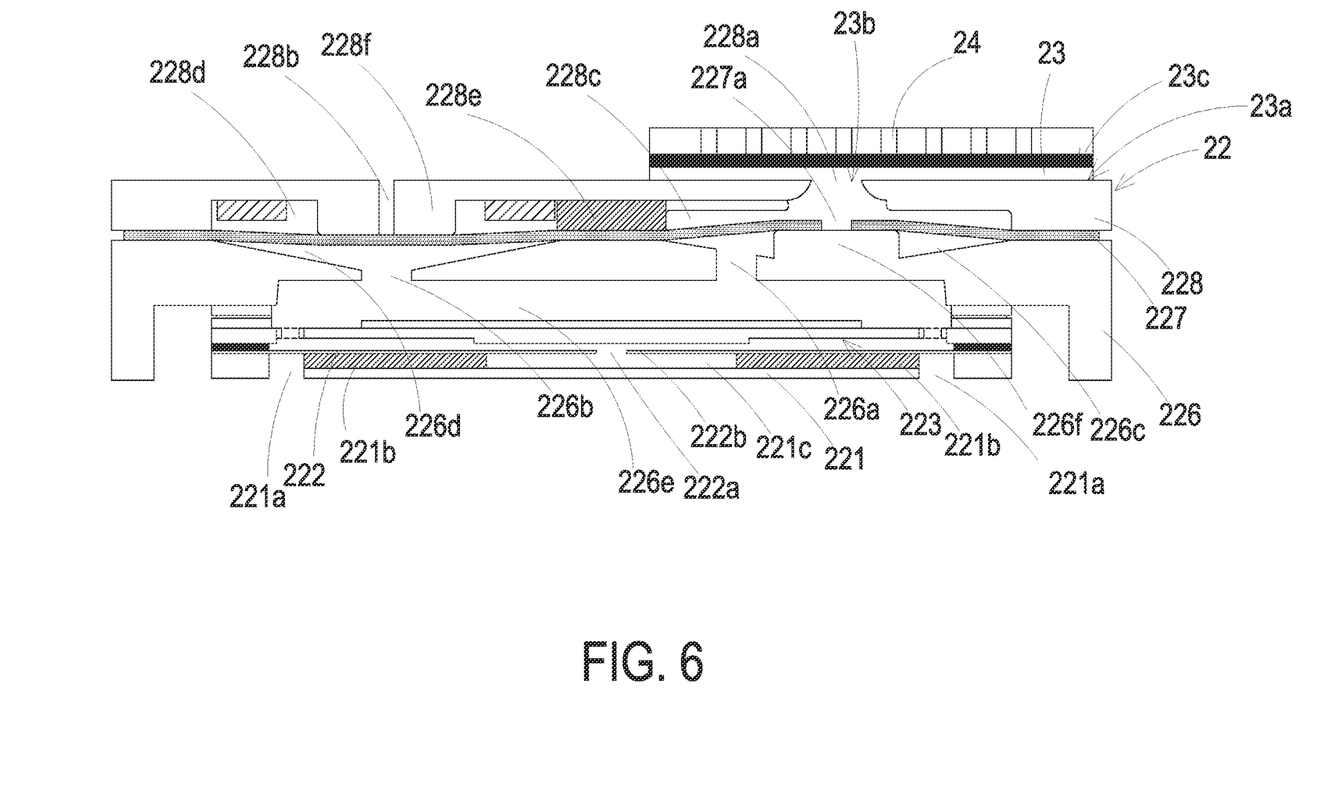
FIG. 6 is a cross sectional view illustrating the micro gas pump combined with the pressure sensor according to an embodiment of the present disclosure.

Please refer to FIGS. 4, 5 and 6. In some embodiments, the micro gas pump 22 is a micro pneumatic device actuated by piezoelectricity. The micro gas pump 22 may include a micro gas transportation device 22A and a micro valve device 22B, which are combined with each other. The micro gas transportation device 22A includes a gas inlet plate 221, a resonance plate 222, a piezoelectric actuator 223, a first insulation plate 2241, a second insulation plate 2242 and a conducting plate 225. The piezoelectric actuator 223 is disposed correspondingly to the resonance plate 222, and the gas inlet plate 221, the resonance plate 222, the piezoelectric actuator 223, the first insulation plate 2241, the conducting plate 225 and the second insulation plate 2242 are stacked sequentially to be assembled as the micro gas transportation device 22A. The piezoelectric actuator 223 includes a suspension plate 223a and a piezoelectric ceramic plate 223b. The micro valve device 22B includes a gas collecting plate 226, a valve membrane 227 and an outlet plate 228 stacked sequentially, but not limited thereto. The gas collecting plate 226 may be a single plate structure, or a frame structure having sidewalls around the periphery as exemplified in FIG. 5, wherein an accommodation space is commonly defined by the sidewalls and the bottom part of the gas collecting plate 226. Moreover, as shown in FIGS. 5 and 6, the gas inlet plate 221 has at least one inlet aperture 221a, at least one convergence channel 221b and a convergence chamber 221c. The at least one inlet aperture 221a allows gas to flow in. The convergence channel 221b is disposed correspondingly to the inlet aperture 221a and guides the gas from the inlet aperture 221a toward the convergence chamber 221c. The resonance plate 222 has a central aperture 222a corresponding in position to the convergence chamber 221c. The resonance plate 222 further includes a movable part 222b surrounding the central aperture 222a. The piezoelectric actuator 223 and the resonance plate 222 are disposed facing each other. A gap is formed between the resonance plate 222 and the piezoelectric ceramic plate 223b of the piezoelectric actuator 223, so that when the piezoelectric actuator 223 is driven, the gas is inhaled through at least one inlet aperture 221a of the gas inlet plate 221, converged to the convergence chamber 221c along the convergence channel 221b and transported into the gap through the central aperture 222a of the resonance plate 222. Whereby, the gas is further transported through a resonance between the piezoelectric ceramic plate 223b of the piezoelectric actuator 223 and the movable part 222b of the resonance plate 222. A front perspective view of the micro gas pump 22 is illustrated in FIG. 4, wherein the micro gas transportation device 22A is received within the accommodation space of the gas collecting plate 226 and has the bottom stacked on the valve membrane 227 and the outlet plate 228. Further as shown in FIGS. 5 and 6, the outlet plate 228 of the micro valve device 22B has a gas-collecting perforation 228a and a pressure-releasing perforation 228b, and has a first gas-collecting chamber 228c and a first pressure-releasing chamber 228d concavely formed thereon. The gas-collecting perforation 228a is in fluid communication with the first gas-collecting chamber 228c. The pressure-releasing perforation 228b is in fluid communication between the first pressure-releasing chamber 228d and an external environment. A communication channel 228e is formed between the first gas-collecting chamber 228c and the first pressure-releasing chamber 228d, and the first pressure-releasing chamber 228d has a first convex structure 228f. Furthermore, the gas collecting plate 226 includes a plurality of perforations, a second gas-collecting chamber 226c, a second pressure-releasing chamber 226d and a communication slot 226e. The communication slot 226e is in fluid communication with the second gas-collecting chamber 226c and the second pressure-releasing chamber 226d, respectively, through the plurality of perforations. The second gas-collecting chamber 226c is corresponding in position to the first gas-collecting chamber 228c of the outlet plate 228 to form an integrated gas-collecting chamber. The second pressure-releasing chamber 226d is corresponding in position to the first pressure-releasing chamber 228d of the outlet plate 228 to form an integrated pressure-releasing chamber. The plurality of perforations include at least one first perforation 226a and at least one second perforation 226b. The first perforation 226a is in fluid communication between the second gas-collecting chamber 226c and the communication slot 226e. The second perforation 226b is in fluid communication between the second pressure-releasing chamber 226d and the communication slot 226e. The second gas-collecting chamber 226c has a second convex structure 226f. The valve membrane 227 is disposed between the gas collecting plate 226 and the outlet plate 228 and has a valve aperture 227a corresponding in position to the gas-collecting perforation 228a of the outlet plate 228. The valve membrane 227 is abutted continuously by the second convex structure 226f to form a pre-force to seal the valve aperture 227a completely. With the micro gas transportation device 22A and the micro valve device 22B assembled, and the elastic medium 23 mounted on the micro gas pump 22 and covering and sealing the gas-collecting perforation 228a of the micro gas pump 22, the gas is inhaled through the at least one inlet aperture 221a of the inlet plate 221 of the micro gas transportation device 22A and compressed to flow into the micro valve device 22B by a resonance of the piezoelectric actuator 223 occurred in the communication slot 226e. In this way, the gas flows in a single direction in the micro valve device 22B, passes through the valve aperture 227a of the valve membrane 227 and is transported into the first gas-collecting perforation 228a of the outlet plate 228. Thus, the gas is converged to the elastic medium 23 in fluid communication with the gas-collecting perforation 228a, so that a pressurizing operation is performed. Alternatively, in case of a pressure-releasing operation, the micro gas transportation device 22A is disabled, and the gas converged in the elastic medium 23 is transported to the pressure-releasing perforation 228b through the communication channel 228e of the outlet plate 228 of the micro valve device 22B and then discharged out, so that the pressure-releasing operation is performed. The actions of the pressurizing operation and the pressure-releasing operation of the micro gas pump 22 of the present disclosure will be detailedly described as follows.

Figure 7A:
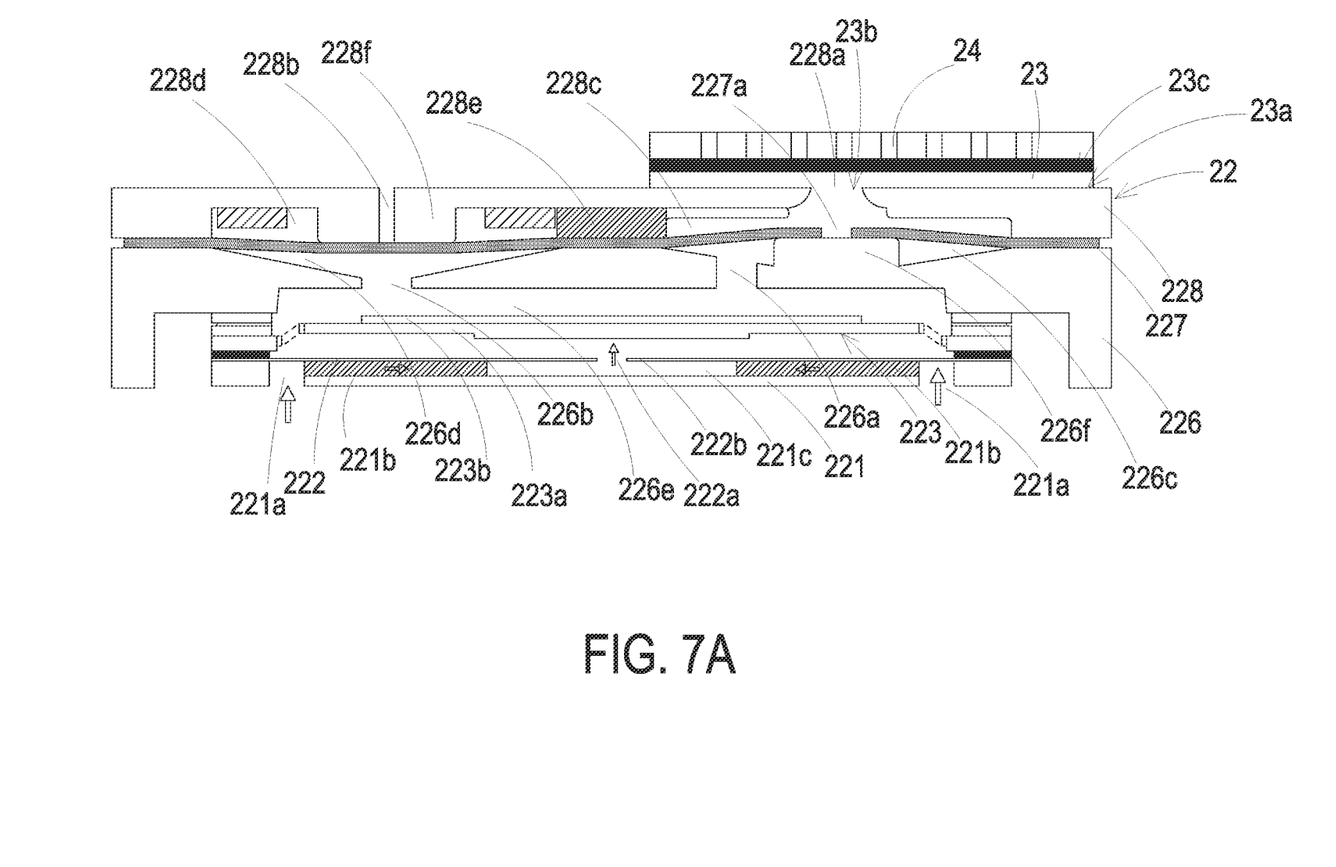
FIGS. 7A to 7D show the actions of the micro gas pump combined with the pressure sensor according to an embodiment of the present disclosure.
Figure 7B:
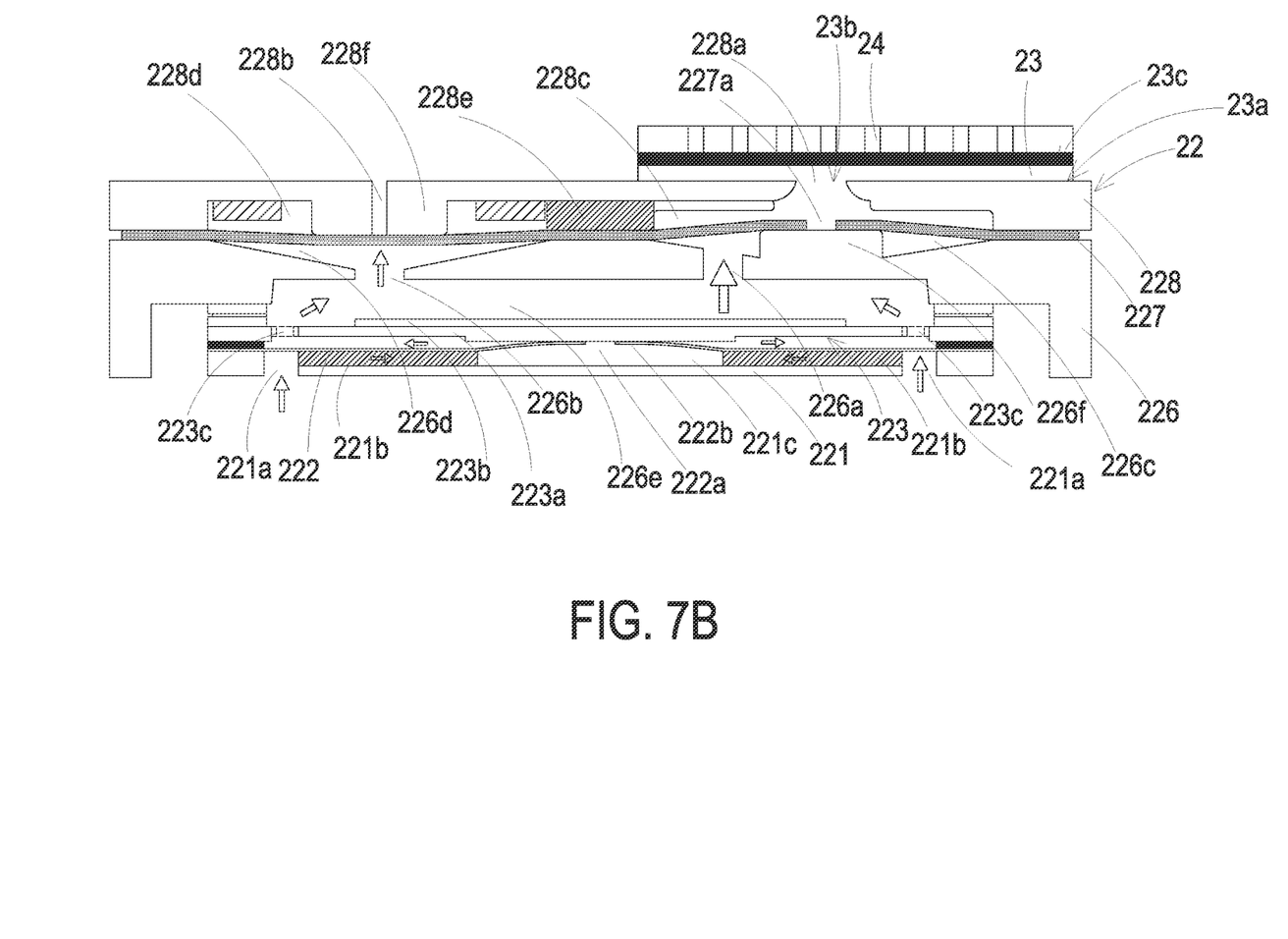
Figure 7C:
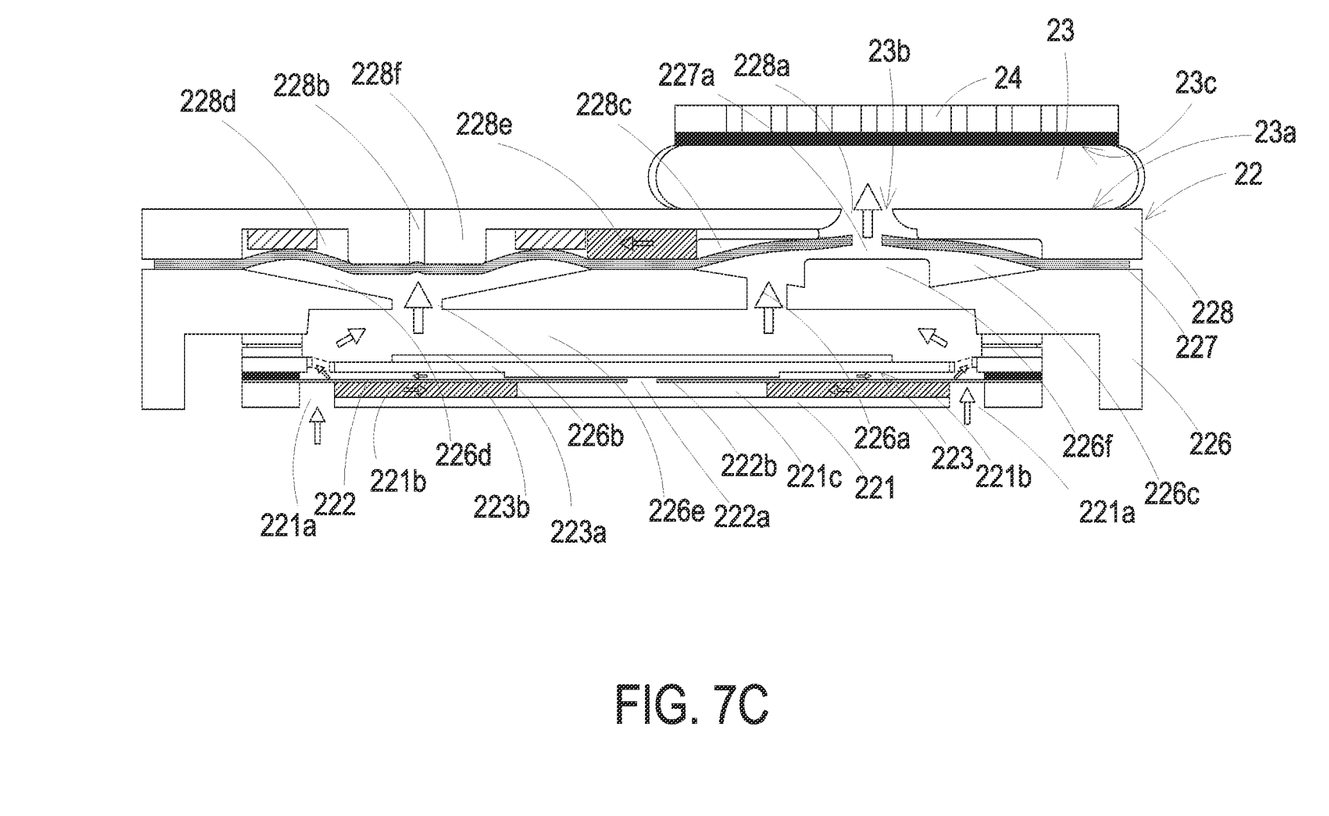
Figure 7D:
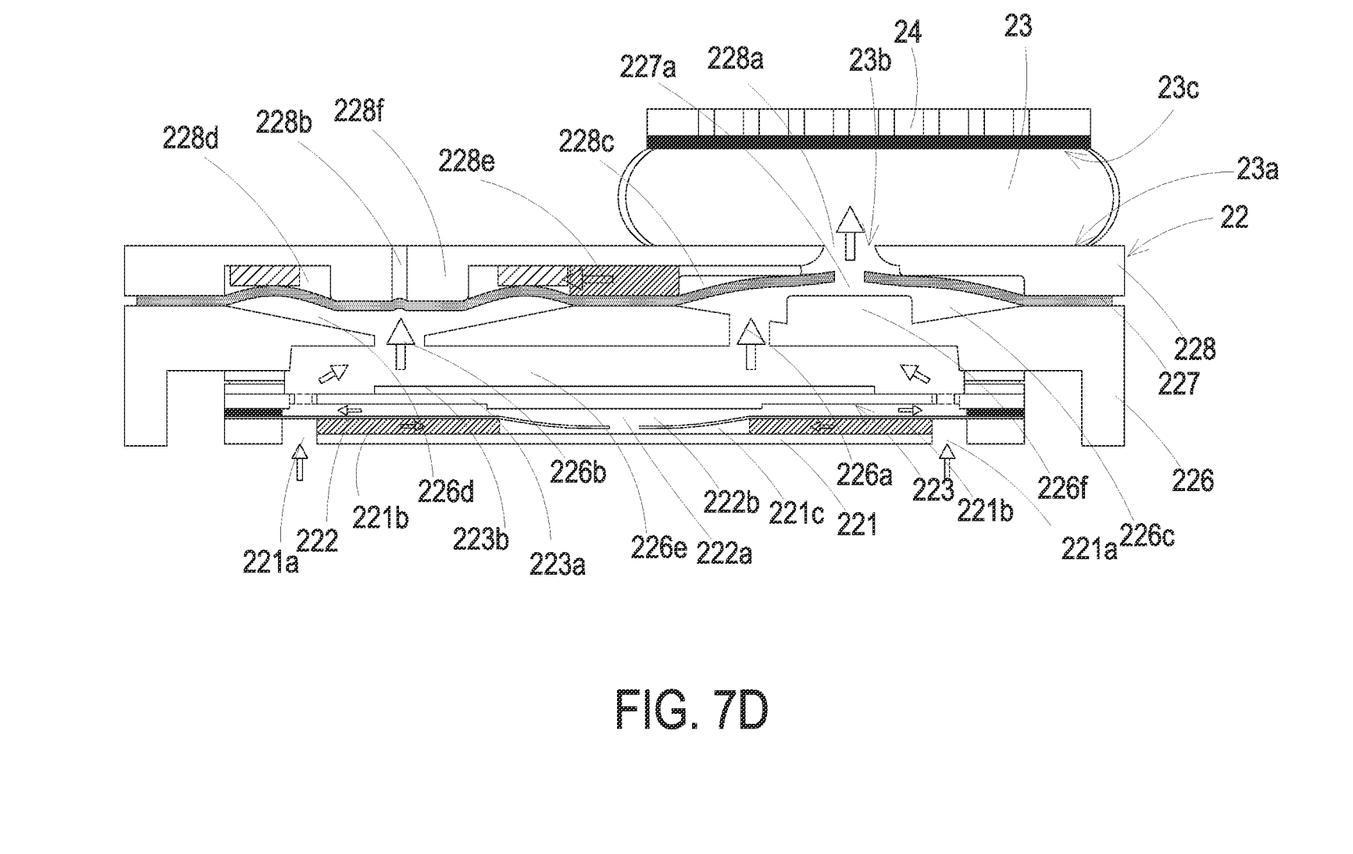
Figure 8:
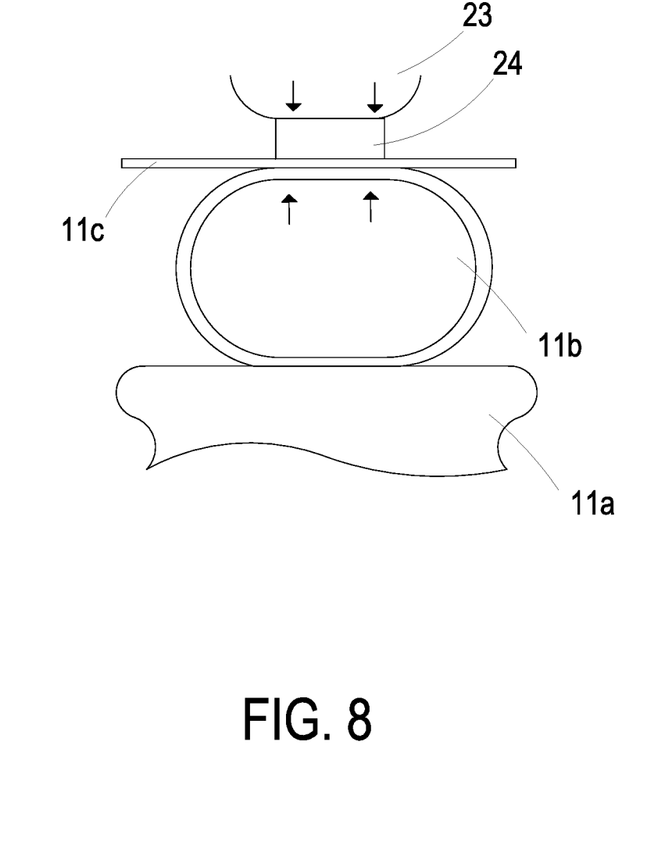
FIG. 8 shows a measuring action of the wearable blood pressure measuring device according to an embodiment of the present disclosure.

Please refer to FIGS. 7A to 7B. When the micro gas pump 22 is enabled, the piezoelectric ceramic plate 223b of the piezoelectric actuator 223 is driven in response to an applied voltage and being deformed by the piezoelectric effect, so that the suspension plate 223a is driven to vibrate and move upwardly and downwardly. Therefore, as shown in FIG. 7A, when the piezoelectric ceramic plate 223b drives the suspension plate 223a of the piezoelectric actuator 223 to move upwardly and away from the resonance plate 222, the volume between the suspension plate 223a and the resonance plate 222 is expanded and the gas tends to be inhaled into the inlet aperture 221a of the gas inlet plate 221. Consequently, the gas is inhaled from the external environment through the inlet aperture 221a and converged into the convergence chamber 221c through the convergence channel 221b to flow into the micro gas pump 22. As shown in FIG. 7B, when the piezoelectric actuator 223 is actuated and the suspension plate 223a moves downwardly and returns to the original position, the movable part 222b of the resonance plate 222 and the suspension plate 223a are close to each other and the gas around the peripheral regions of the suspension plate 223a is compressed to flow into the communication slot 226e of the gas collecting plate 226 through at least one vacant space 223c of the piezoelectric actuator 223. Further as shown in FIG. 7C, when the piezoelectric ceramic plate 223b drives the suspension plate 223a of the piezoelectric actuator 223 to move downwardly, the volume of the communication slot 226e is expanded, and the gas is transported rapidly into the second gas-collecting chamber 226c through the first perforation 226a and into the second pressure-releasing chamber 226d through the second perforation 226b. Under this circumstance, the pressure of the gas pushes the valve membrane 227 to deform upwardly, and the valve aperture 227a is kept away from the pre-force of the second convex structure 226f. Consequently, the second gas-collecting chamber 226c is in fluid communication with the first gas-collecting chamber 228c and the pressure-releasing perforation 228b in fluid communication between the first pressure-releasing chamber 228d and an external environment is abutted by the valve membrane 227 and closed. The gas converged in the communication slot 226e can be transported into the elastic medium 23 through the gas-collecting perforation 228a of the outlet plate 228, so as to accumulate gas pressure. As shown in FIG. 7D, the gas is utilized to fill the volume of the elastic medium 23 so as to push the pressure sensor 24 to be displaced. With the continuous operations of the piezoelectric actuator 223, the gas continues to flow through the gas collecting plate 226, the valve aperture 227a and the pressure-releasing perforation 228b, so as to support the pressure sensor 24 to be raised and able to abut against the specific position of the user for sensing.

From the above, when the wearable blood pressure measuring device 2 of the present disclosure is utilized to measure the blood pressure, as shown in FIGS. 7A to 7D and 8, the elastic medium 23 is inflated by the micro gas pump 22 continuously, and the pressure sensor 24 tends to abut against and contact with the skin 11c of the user, so as to press the artery 11b located between the skin 11c and the bone 11a of the user. Thus, the pressure sensor 24 abuts against the artery 11b of the user and measures the blood pressure of the target artery 11b by flattening and scanning operation. The blood pressure information is transmitted to the driving-and-control module 25.

Figure 9:
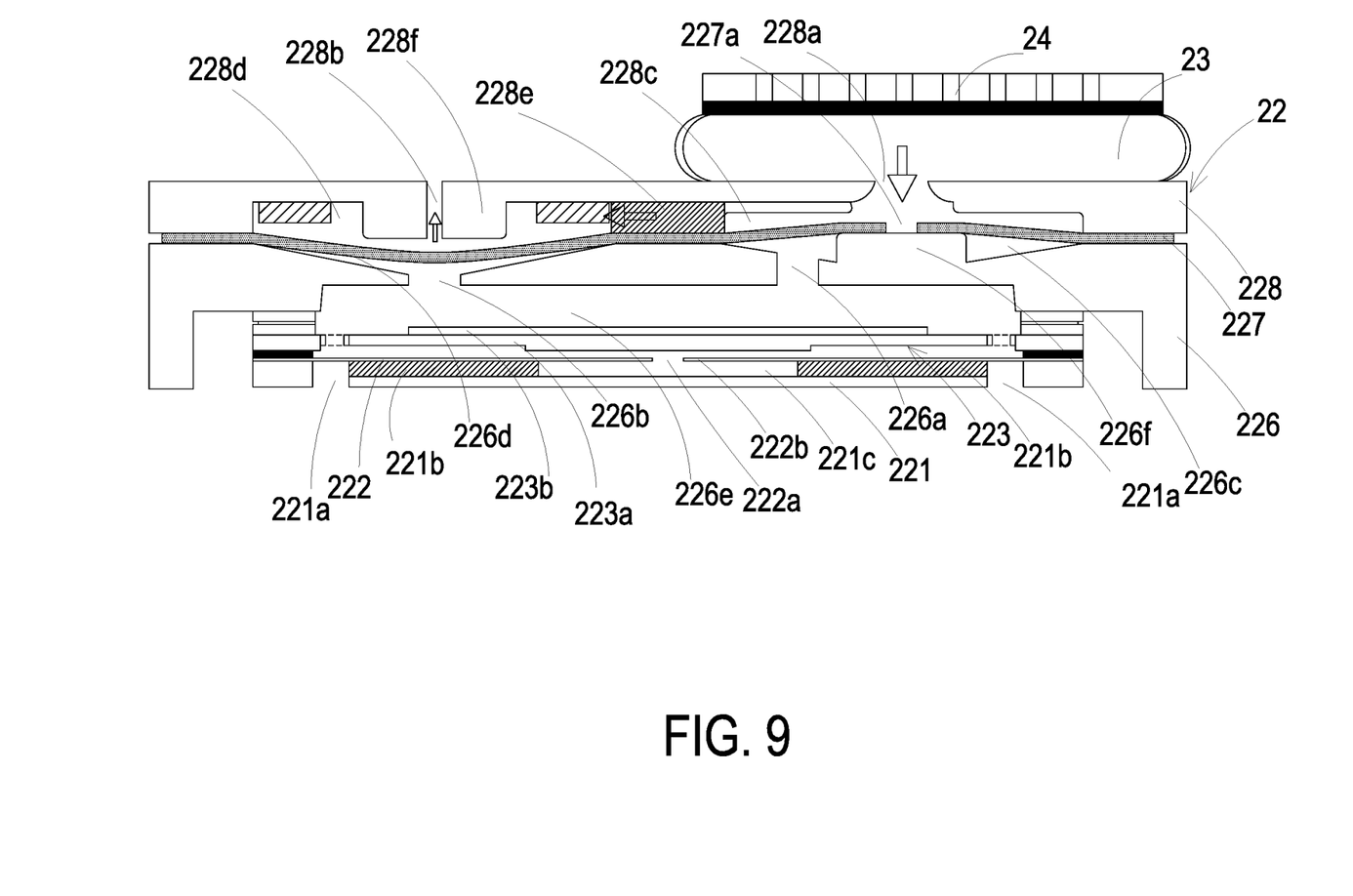
FIG. 9 is a schematic structural view illustrating the wearable blood pressure measuring device to be performed

Please refer to FIG. 9, again. When the measurement of the blood pressure is completed, the micro gas pump 22 is disabled. Under this circumstance, the inner pressure of the elastic medium 23 is higher than that of the micro gas pump 22, and the gas tends to flow from the elastic medium 23 to the micro gas pump 22. When the gas flows into the micro gas pump 22, the gas converged in the outlet plate 228 pushes the valve membrane 227. In this way, the valve aperture 227a of the valve membrane 227 is moved downwardly to abut against the second convex structure 226f of the gas collecting plate 226 so as to close the valve aperture 227a and prevent the gas from reversely flowing to the gas collecting plate 226. At the same time, the valve membrane 227 covering the pressure-releasing perforation 228b is away from the position that the valve membrane 227 is abutting against the pressure-releasing perforation 228b, so as to open the pressure-releasing perforation 228b. In this way, the gas converged in the elastic medium 23 is transported through the gas-collecting perforation 228a and the communication channel 228e, into the pressure-releasing perforation 228b, and then discharged out from the pressure-releasing perforation 228b. Consequently, the pressure-releasing operation is completed.

In the embodiment, the transmission module 251 is disposed on the driving-and-control module 25 (as shown in FIG. 3) to transmit the measured blood pressure information to an external device (not shown). The blood pressure information can be utilized for further analysis and statistics, so as to understand the health situation of the user well. The disposition of the transmission module 251 is not limited thereto and can be adjustable according to the practical requirements. In some embodiments, the transmission module 251 can be a wired transmission module, for example USB, mini-USB or micro-USB, but not limited thereto. In some other embodiments, the transmission module 251 can be a wireless transmission module, for example a Wi-Fi module, a Bluetooth module, a radio frequency identification (RFID) module or a near field communication (NFC) module, but not limited thereto. In further some other embodiments, the transmission module 251 can include the wired transmission module and the wireless transmission module at the same time. Moreover, the data transmission means can be adjustable according to the practical requirements. Any implementation of storing the physiological information of the user wearing the wearable blood pressure measuring device 2 in the driving-and-control module 25 is included in the claimed scope of the present disclosure, and not redundantly described hereinafter. Furthermore, the external device can be for example but not limited to a cloud system, a portable device or a computer system. The external device is mainly utilized to receive the transmitted physiological information of the user wearing the wearable blood pressure measuring device 2 of the present disclosure, and the physiological information can be further analyzed and compared by a program, so as to understand the health condition of the user well.

In summary, the present disclosure provides a wearable blood pressure measuring device having a micro gas pump, an elastic medium and a pressure sensor combined together. By transporting gas to the elastic medium through a piezoelectrically actuated micro gas pump, the elastic medium is inflated with gas and expanded to raise the pressure sensor, so that the pressure sensor abuts against the skin of the user. Then, the pressure sensor measures the blood pressure information of the user. The blood pressure information is transmitted to a driving-and-control module and further transmitted to an external device or displayed directly by a display screen. Thus, it benefits to achieve the effect of precise measurement at anytime and anywhere. In addition, the wearable blood pressure measuring device can achieve the advantages of small size, light weight, convenience for users to carry and energy saving. Therefore, the wearable blood pressure measuring device of the present disclosure is highly industrially utilized, so as to file a patent application.

While the disclosure has been described in terms of what is presently considered to be the most practical and preferred embodiments, it is to be understood that the disclosure needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A wearable blood pressure measuring device comprising:
a strap structure adapted to be worn by a user and having an outer surface and an inner surface;
a micro gas pump embedded within the strap structure; and
a pressure sensor combined with the micro gas pump through an elastic medium, wherein the elastic medium is sandwiched between the micro gas pump and the pressure sensor and has a first surface and a second surface, and the first surface has an opening communicating with a gas-collecting perforation of the micro gas pump, whereby gas is guided into the elastic medium from the micro gas pump, and the pressure sensor is disposed on the second surface opposite to the first surface and configured to be in contact with skin of the user for monitoring blood pressure;

wherein the micro gas pump is operated to drive gas to be transported into the elastic medium, whereby the elastic medium is inflated with the gas, so the pressure sensor is configured to push against the skin of the user, and to measure a blood pressure of a target artery by a flattening and scanning operation.

2. The wearable blood pressure measuring device according to claim 1, wherein the micro gas pump is a piezoelectrically actuated micro pneumatic device comprising a micro gas transportation device and a micro valve device, wherein the gas is transported from the micro gas transportation device to the micro valve device so that a pressurizing operation or a pressure-releasing operation is performed.

3. The wearable blood pressure measuring device according to claim 2, wherein the micro gas transportation device comprises:
   a gas inlet plate having at least one inlet aperture, at least one convergence channel and a convergence chamber, wherein the at least one inlet aperture allows gas to flow in, and the convergence channel is disposed correspondingly to the inlet aperture and guides the gas from the inlet aperture toward the convergence chamber;
   a resonance plate having a central aperture and a movable part, wherein the central aperture is aligned with the convergence chamber and the movable part surrounds the central aperture; and
   a piezoelectric actuator facing the resonance plate and assembled by a suspension plate and a piezoelectric ceramic plate, wherein a gap is formed between the resonance plate and the piezoelectric actuator, wherein when the piezoelectric actuator is driven, the gas is introduced into the at least one inlet aperture of the gas inlet plate, converged to the convergence chamber along the at least one convergence channel, and flows into the gap through the central aperture of the resonance plate, whereby the gas is further transported through a resonance between the piezoelectric actuator and the movable part of the resonance plate.

4. The wearable blood pressure measuring device according to claim 3, wherein the micro gas transportation device further comprises a conducting plate, a first insulation plate and a second insulation plate, wherein the gas inlet plate, the resonance plate, the piezoelectric actuator, the first insulation plate, the conducting plate and the second insulation plate are stacked sequentially.

5. The wearable blood pressure measuring device according to claim 2, wherein the micro valve device comprises:
   an outlet plate having a pressure-releasing perforation, a first gas-collecting chamber and a first pressure-releasing chamber concavely formed thereon, wherein the gas-collecting perforation is in fluid communication with the first gas-collecting chamber and the elastic medium covers an end of the gas-collecting perforation, wherein the pressure-releasing perforation is in fluid communication between the first pressure-releasing chamber and an external environment, wherein a communication channel is formed between the first gas-collecting chamber and the first pressure-releasing chamber, and the first pressure-releasing chamber has a first convex structure;
   a gas collecting plate having a plurality of perforations, a second gas-collecting chamber, a second pressure-releasing chamber and a communication slot, wherein the communication slot is in fluid communication with the second gas-collecting chamber and the second pressure-releasing chamber through the plurality of perforations, the second gas-collecting chamber corresponds in position to the first gas-collecting chamber of the outlet plate to form an integrated gas-collecting chamber, the second pressure-releasing chamber corresponds in position to the first pressure-releasing chamber of the outlet plate to form an integrated pressure-releasing chamber, and the plurality of perforations includes a first perforation and a second perforation, wherein the first perforation is in fluid communication between the second gas-collecting chamber and the communication slot, the second perforation is in fluid communication between the second pressure-releasing chamber and the communication slot, and the second gas-collecting chamber has a second convex structure; and
   a valve membrane disposed between the gas collecting plate and the outlet plate, and having a valve aperture corresponding in position to the gas-collecting perforation of the outlet plate, wherein the valve membrane is abutted continuously by the second convex structure to form a pre-force;
   wherein when the gas is transported from the micro gas transportation device to the micro valve device, the gas is transported into the elastic medium through the gas-collecting perforation of the outlet plate to perform the pressurizing operation, wherein when the gas ceases being transported from the micro gas transportation device to the micro valve device, the gas is discharged through the pressure-releasing perforation of the outlet plate to perform the pressure-releasing operation.

6. The wearable blood pressure measuring device according to claim 1 further comprising a driving-and-control module comprising a controlling circuitry, the driving-and-control module disposed on the strap structure for controlling the micro gas pump.

7. The wearable blood pressure measuring device according to claim 6, wherein the driving-and-control module further comprises a display screen for displaying information of the blood pressure measured by the pressure sensor.

8. The wearable blood pressure measuring device according to claim 6 further comprising a transmission module disposed on the driving-and-control module to transmit information of the blood pressure of the user wearing the wearable blood pressure measuring device to an external device, wherein the transmission module is at least one selected from the group consisting of a wired transmission module and a wireless transmission module, the wired transmission module is at least one selected from the group consisting of USB, mini-USB and micro-USB, and the wireless transmission module is at least one selected from the group consisting of a Wi-Fi module, a Bluetooth module, a radio frequency identification module and a near field communication module.

9. The wearable blood pressure measuring device according to claim 8, wherein the external device is at least one selected from the group consisting of a cloud system, a portable device and a computer system.

10. The wearable blood pressure measuring device according to claim 1, wherein the elastic medium is an airbag.

* * * * *